(12) United States Patent
Stowell et al.

(10) Patent No.: US 6,492,556 B2
(45) Date of Patent: *Dec. 10, 2002

(54) FORM A OF FLUOXETINE HYDROCHLORIDE

(76) Inventors: Grayson Walker Stowell, 710 Darwin Dr., Wilmington, NC (US) 28405; Robert R. Whittle, 5006 Pine Needles Dr., Wilmington, NC (US) 28403

( * ) Notice: Subject to any disclaimer, the term of this patent is extended or adjusted under 35 U.S.C. 154(b) by 0 days.

This patent is subject to a terminal disclaimer.

(21) Appl. No.: 09/991,839

(22) Filed: Nov. 5, 2001

(65) Prior Publication Data

US 2002/0169341 A1 Nov. 14, 2002

Related U.S. Application Data

(63) Continuation of application No. 09/772,969, filed on Jan. 31, 2001, now Pat. No. 6,316,672.

(51) Int. Cl.[7] .............................................. C07C 213/00
(52) U.S. Cl. ..................................................... 564/347
(58) Field of Search ......................................... 564/347

(56) References Cited

U.S. PATENT DOCUMENTS

| 4,296,126 A | 10/1981 | Nedelac et al. ............. 424/316 |
|---|---|---|
| 4,314,081 A | 2/1982 | Molloy et al. ............... 564/347 |
| 4,584,404 A | 4/1986 | Molloy et al. ............... 564/347 |
| 4,626,549 A | 12/1986 | Molloy et al. ............... 514/651 |
| 5,068,432 A | 11/1991 | Brown ........................ 564/347 |
| 5,104,899 A | 4/1992 | Young et al. ................ 514/646 |
| 5,166,437 A | 11/1992 | Kairisalo et al. ............ 564/347 |
| 5,225,585 A | 7/1993 | Schwartz et al. ............ 558/275 |
| 5,238,959 A | 8/1993 | Robertson et al. ........... 514/604 |
| 5,250,571 A | 10/1993 | Fuller et al. ................. 514/651 |
| 5,589,511 A | 12/1996 | Young et al. ................ 514/646 |
| 5,618,968 A | 4/1997 | Crnic et al. .................... 560/27 |
| 5,648,396 A | 7/1997 | Young et al. ................ 514/651 |
| 5,708,035 A | 1/1998 | Young et al. ................ 514/649 |
| 5,847,214 A | 12/1998 | Arosio et al. ................ 564/347 |
| 5,936,124 A | 8/1999 | Hilborn et al. .............. 564/347 |
| 6,025,517 A | 2/2000 | Hilborn et al. ................ 560/27 |
| 6,028,224 A | 2/2000 | Hilborn et al. .............. 564/347 |
| 6,258,853 B1 | 7/2001 | Stowell et al. .............. 514/651 |
| 6,310,250 B1 | 10/2001 | Stowell et al. .............. 564/347 |
| 6,310,251 B1 | 10/2001 | Stowell et al. .............. 564/347 |
| 6,316,672 B1 * | 11/2001 | Stowell et al. .............. 564/347 |

FOREIGN PATENT DOCUMENTS

| EP | 0 391 070 B1 | 1/1994 | ......... C07C/217/62 |
|---|---|---|---|
| EP | 0 529 842 B1 | 4/1996 | ......... C07C/213/06 |
| GB | 2060618 | 5/1981 | ........... C07C/93/14 |
| WO | WO 94/00416 | 1/1994 | |
| WO | WO 98/11054 | 3/1998 | ......... C07C/213/08 |
| WO | WO 99/49857 | 10/1999 | ......... A61K/31/135 |

OTHER PUBLICATIONS

Chem Abstract 1988: 37309, abstract of J.Med.Chem. 1988, 31(1), 185–189, Robertson et al.
J.Med.Chem. 1988 31(1), 185–189, Robertson et al.
U.S. Application No. 09/772,969, Stowell et al., *Form A of Fluoxetine Hydrochloride*, Filed Jan. 31, 2001.
U.S. Application No. 09/772,968, Stowell et al., *Form A of Fluoxetien Hydrochloride*, Filed Jan. 31, 2001.

* cited by examiner

*Primary Examiner*—Samuel Barts
(74) *Attorney, Agent, or Firm*—Myers Bigel Sibley & Sajovec, PA

(57) ABSTRACT

The present invention relates to novel polymorphic Form A of fluoxetine hydrochloride.

1 Claim, 11 Drawing Sheets

US 6,492,556 B2

FORM A OF FLUOXETINE HYDROCHLORIDE

CROSS-REFERENCE TO RELATED APPLICATIONS

The present application is a continuation application of Ser. No. 09/772,969 filed Jan. 31, 2001, now U.S. Pat. No. 6,316,672, the disclosure of which is incorporated herein by reference in its entirety.

The present invention is generally concerned with a novel polymorphic form of fluoxetine hydrochloride, (±)-N-methyl-3-phenyl-2-[$\alpha,\alpha,\alpha$-trifluoro-p-tolyl) oxy] propylamine hydrochloride, which is marketed by Dista Products and Eli Lilly and Company (the "Innovator"), Indianapolis, Ind., under the trade name Prozac®. The present invention is further concerned with the preparation and use of the polymorphic form of fluoxetine hydrochloride now designated Form A ("Form A").

Polymorphic forms of the same drug substance (also known as the active pharmaceutical ingredient or "API"), as administered by itself or formulated as a drug product (also known as the final or finished dosage form) are well known in the pharmaceutical art to affect, for example, the solubility, stability, flowability, fractability, and compressibility of drug substances and the safety and efficacy of drug products, (see, e.g. Knapman, K. *Modern Drug Discoveries*, March, 2000: 53). So critical are the potential effects of different polymorphic forms in a single drug substance on the safety and efficacy of the respective drug product(s) that the United States Food and Drug Administration (the "FDA") requires each drug substance manufacturer, in the least, to control its synthetic processes such that the percentages of the various respective polymorphic forms, when present, must be consistent among batches and within the drug substance/product's specification as approved by the FDA.

Left uncontrolled in synthetic processes, the percentage of a given polymorph outside of an FDA approved specification would render the adulterated batches unfit for commercial sale. Accordingly, the FDA requires fall characterization of each drug substance used in each drug product marketed in the United States, including the identification and control of polymorphic forms. The FDA further requires robust synthetic process specifications and controls which consistently produce the respective drug substance and drug product. Unfortunately, the detection of various polymorphic forms of a single drug substance is not always readily discernable by pharmaceutical chemists. Such a drug substance would not be manufactured with appropriate controls, potentially leaving the attendant safety and efficacy risks unaddressed.

It has been discovered that fluoxetine hydrochloride drug substance, generally used to prepare Prozac® and potential generic drugs thereto (fluoxetine hydrochloride API), has not been fully or completely characterized. It has been unexpectedly discovered that such fluoxetine hydrochloride API drug substance comprises at least three crystalline forms, which occur at varying and uncontrolled ratios from batch to batch. These three identified polymorphs have been designated Form A, Form B, and Form C, correlated to the relative proportion of each polymorph in fluoxetine hydrochloride, from greatest to least.

It has further been discovered that Form A can be prepared in pure or essentially pure polymorphic form in robust, controllable, synthetic processes.

DETAILED DESCRIPTION OF THE DRAWINGS

DETAILED DESCRIPTION OF THE INVENTION

Figure 1:
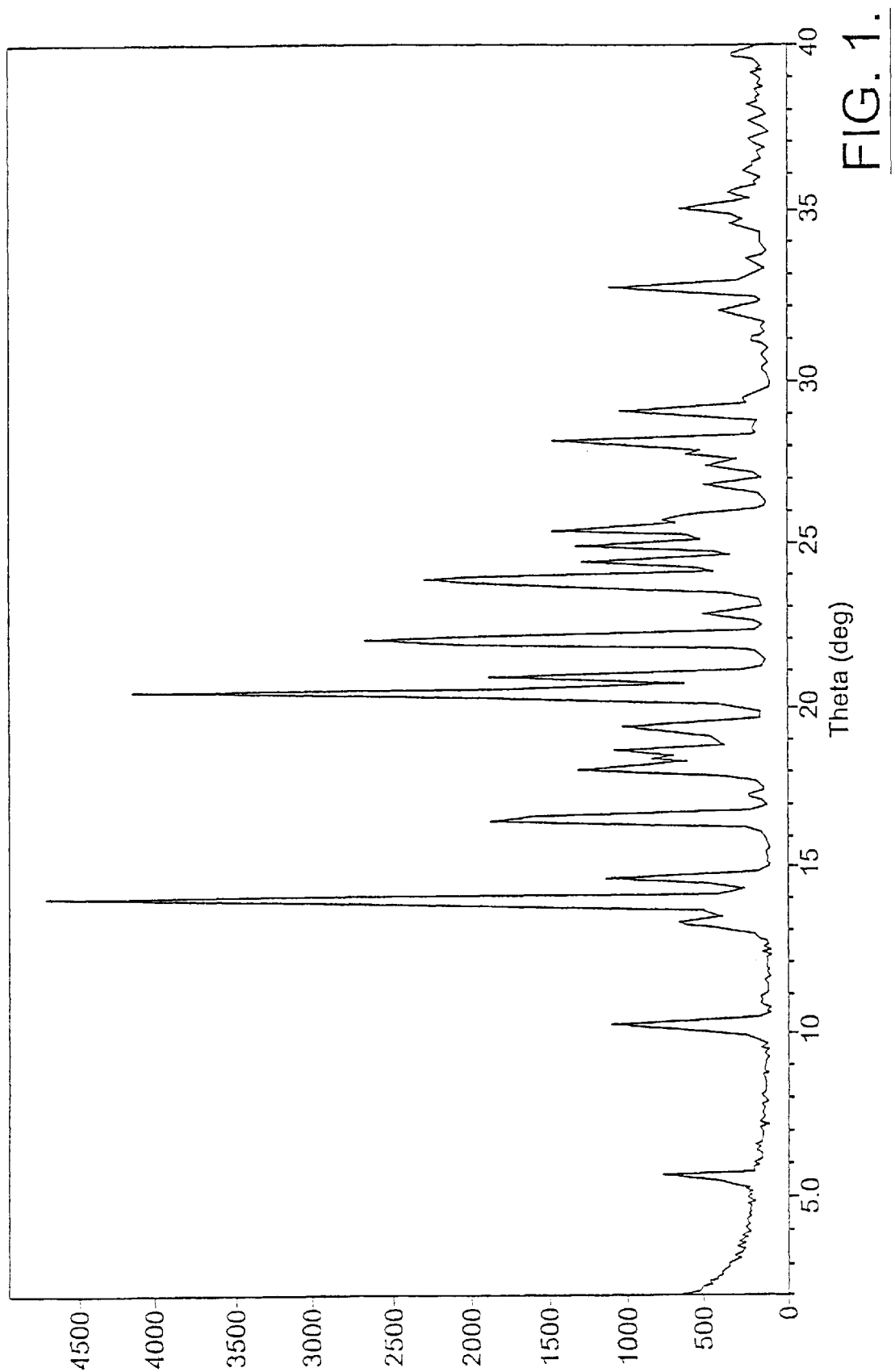
FIG. 1 shows an X-ray powder diffraction (XRD) pattern for fluoxetine hydrochloride API (Lot 1).

The existence of the various polymorphic forms of fluoxetine hydrochloride can not be discerned from the crystallographic literature. More particularly, literature (Robertson, D. W.; Jones, N. D.; Swartzendruber, J. K.; Yang, K. S.; Wong, D. T. *J. Med. Chem.* (1988), 31, 185) reports the crystal structure of fluoxetine hydrochloride API performed at Lilly Research Laboratories. This article details the crystal structure and parameters associated with the structural analysis. The structure was solved in a non-standard setting (Pcab) of the standard Space Group Pbca (#61) and refined to a final R of 0.074. We have independently also solved the identical structure using the standard setting of Pbca (#61) and have refined the structure to a final R of 0.038. Generation of a simulated powder pattern from the crystallographic data reveals a pattern similar to the pattern that Lilly submitted to the International Center for Diffraction Data (ICDD) for inclusion as file #36-1895 in its powder diffraction database [Orthorhombic, Pcab, 10.457× 10.387×32.345 Å]. However, the ICDD database also lists a second file (#44-1517) for fluoxetine hydrochloride. This file was taken from diffraction data presented by Risley, D.; Bopp, R. *Anal. Profiles Drug Subst.*, (1990), 19, and indexed by the editor of ICDD [Orthorhombic, 10.448×14.797× 32.329 Å]. When actual X-ray powder diffraction was performed using a zero background sample mount on the same crystalline material used for single crystal analysis, the measured pattern was found to match ICDD file #44-1517. The crystals were platelets and zero background sample mounts can induce preferred orientations to a powder pattern. To test this, the respective sample was lightly ground to a more uniform size and shape and front packed in an aluminum sample well to produce a random distribution, and reanalyzed by X-ray powder diffraction. The pattern now matches #36-1895, consistent with the structural analysis indicating that patterns #36-1895 and #44-1517 in the ICDD database are the same crystalline phase and differ only by severe preferred orientation problems. Closer examination of the two ICDD patterns show they exhibit extremely similar "d" spacings and unit cell constants which differ only in the b-axis length Indexing of ICDD pattern #36-1895 was based upon single crystal analysis and pattern #44-1517 by indexing from powder diffraction. Indexing (3-D data) from powder diffraction data (2-D data) is considered inconsistent at best, and in this case, appears to have problems. Based upon the axial lengths of 10.457 and 10.387 Å from #36-1895, a special transformation exists. This type of transformation converts the axes to a C-centered cell by using the diagonal of the orthogonal a and b axes, and would generate a cell length of about 14.74 Å for the diagonal (square root of the sum of the squares of the a and b axes) which was assigned to the b-axis. Therefore, the two patterns listed for fluoxetine hydrochloride in the ICDD database are actually the same, differing only in severe preferred orientation Neither sample even remotely suggests that multiple fluoxetine hydrochloride polymorphs exist. In fact, a combination of analytical tools were required to discover the existence of multiple polymorphic forms of fluoxetine hydrochloride and to confirm that Form A was successfully prepared in pure and essentially pure form.

Using the procedure taught in Example 14 herein, Form A of fluoxetine hydrochloride is characterized by the following single crystallographic parameters:

| | |
|---|---|
| crystal class | orthorhombic |
| space group | Pbca (#61) |
| a (521) | 10.3754 (4) |
| b (Å) | 10.4603 (2) |
| c (Å) | 32.3412 (12) |
| V (Å$^3$) | 3510.0 (3) |
| D calc (g/cm$^3$) | 1.31 |
| R, R$_w$ | 0.038, 0.038 |

Figure 3:
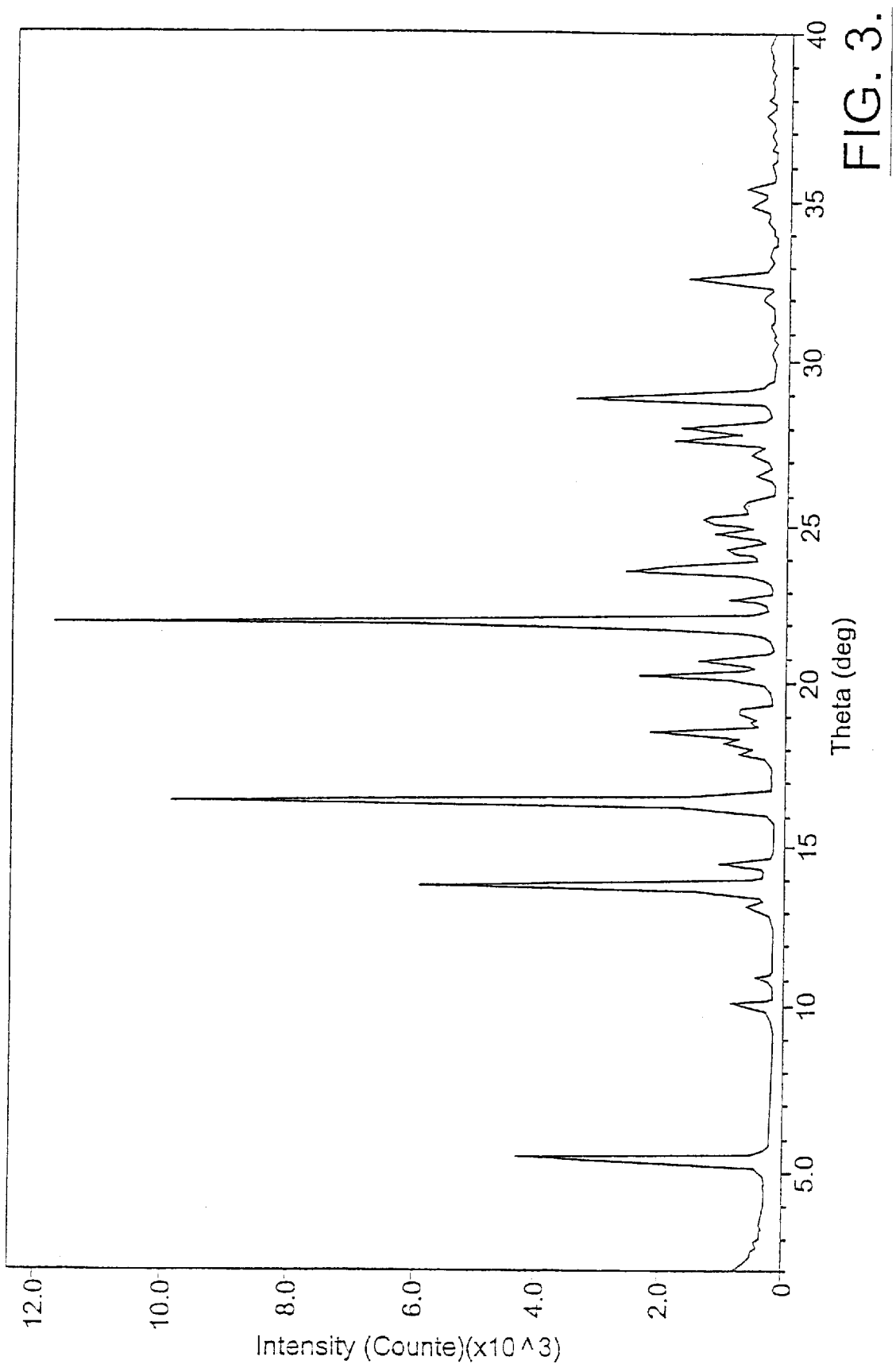
FIG. 3 shows another XRD pattern for fluoxetine hydrochloride API (Lot 2).
Figure 5:
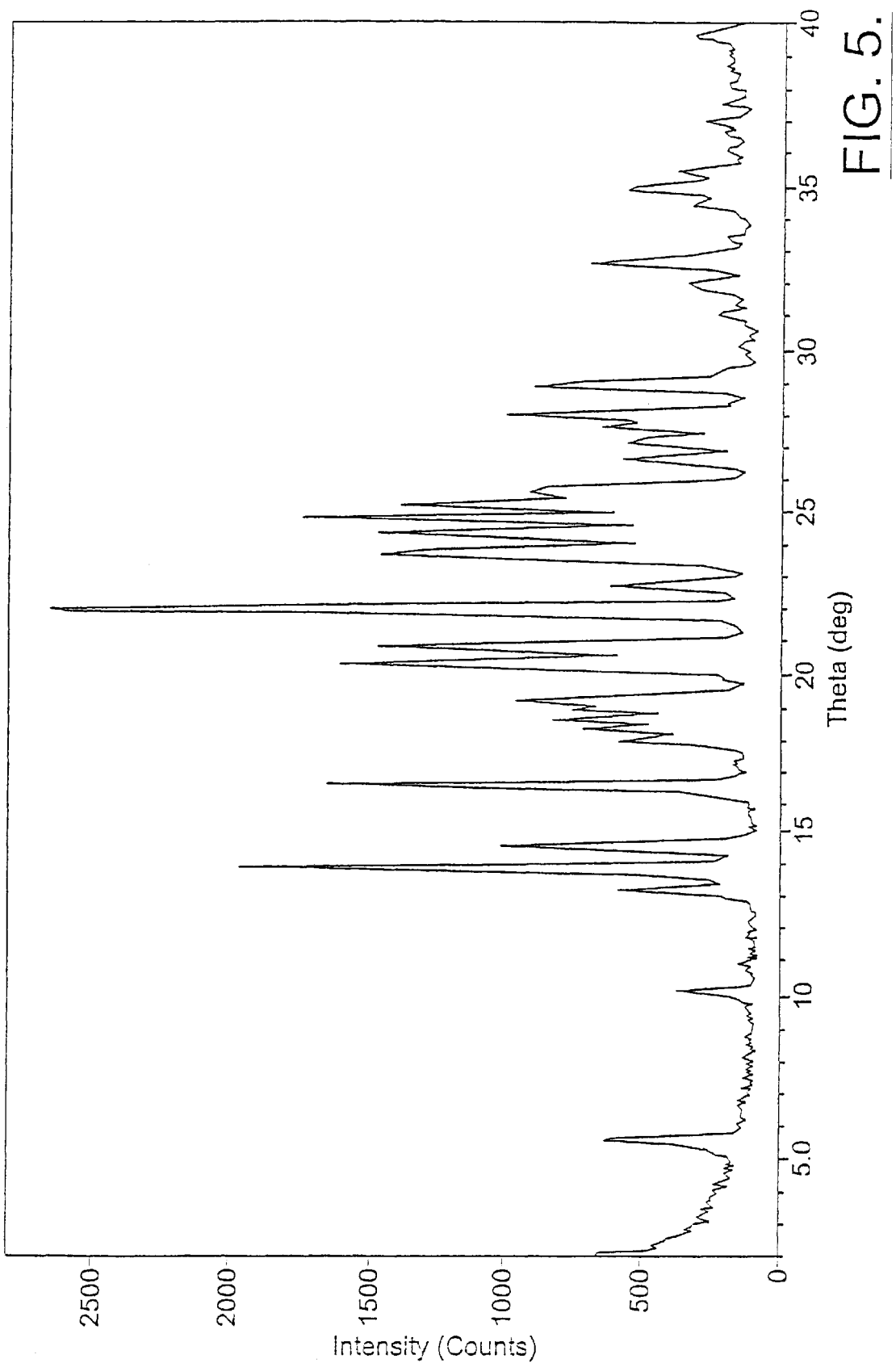
FIG. 5 shows an XRD pattern for pure Form A of fluoxetine hydrochloride prepared via the compression method of preparation taught herein.
Figure 7:
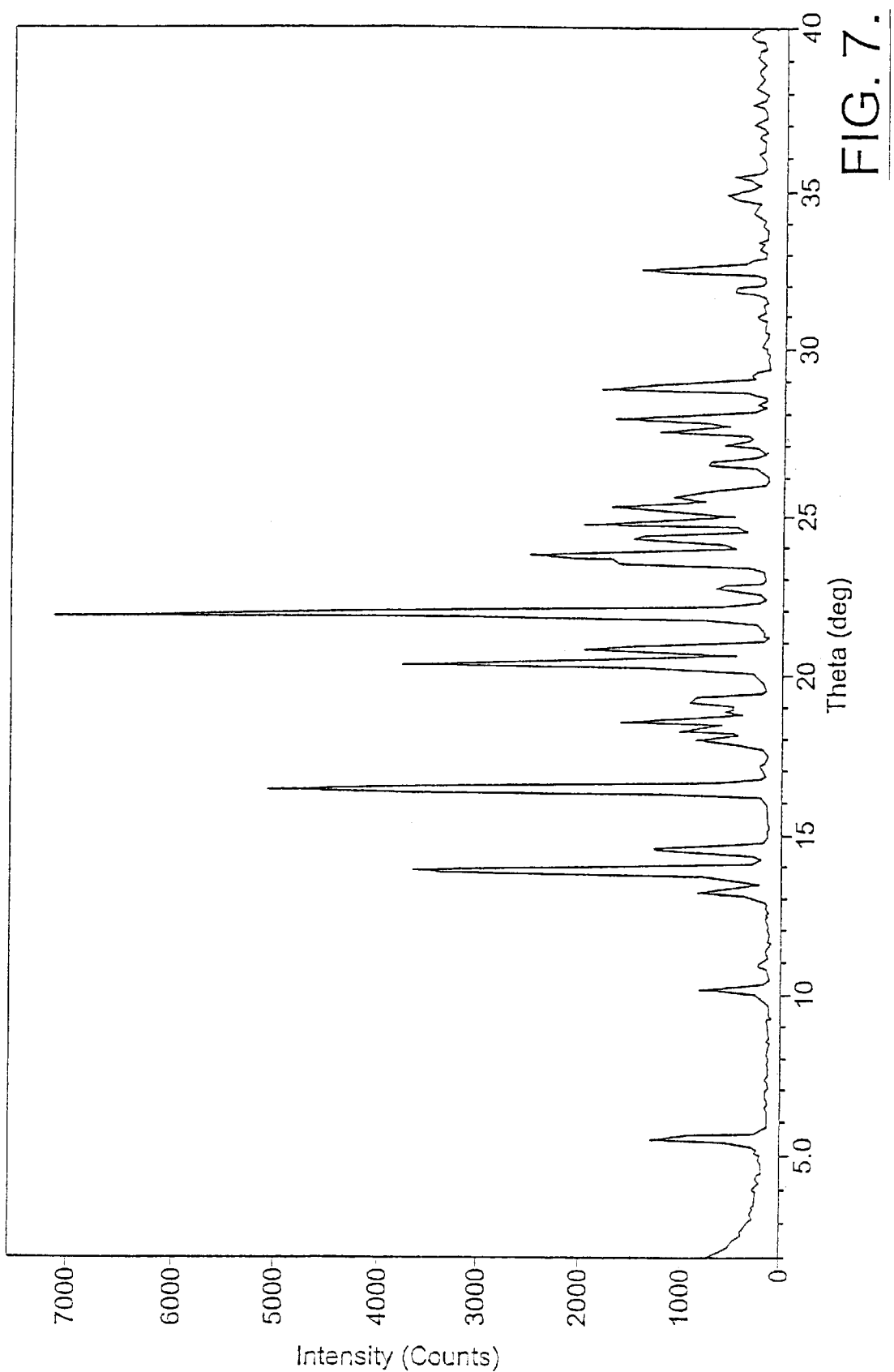
FIG. 7 shows an XRD pattern for pure Form A of fluoxetine hydrochloride prepared via the slurry method of preparation taught herein.

X-ray powder diffraction is another tool typically available for the characterization of mixtures of polymorphs and individual polymorphs of the same substance. However, visual review of powder patterns for fluoxetine hydrochloride API samples (FIGS. 1 and 3) are indistinguishable from Form A powder patterns (FIGS. 5 and 7). When such powder patterns are expressed in terms of "d" spacings and relative intensities, only slight differences among samples are observed (Table 1 below) and are attributable to the sample height packing within the sample holder ("d" spacings) and preferred orientations (relative intensities).

TABLE 1

X-Ray Powder Diffraction

| Lot 1 API[1] | | Lot 2 API[1] | | Compression[2] | | Method Slurry[2] | |
|---|---|---|---|---|---|---|---|
| d (Å) | I[3] | d (Å) | I[3] | d (Å) | I[3] | d (Å) | I[3] |
| 15.68 | w | 16.12 | m | 15.89 | w | 15.93 | w |
| 8.62 | w | 8.77 | w/vw | 8.64 | w/vw | 8.67 | w/vw |
| 6.63 | w/vw | 6.71 | vw | 6.65 | w | 6.67 | w/vw |
| 6.32 | vs | 6.39 | s | 6.33 | s/vs | 6.35 | s |
| 6.04 | w | 6.10 | w/vw | 6.04 | m | 6.06 | w |
| 5.36 | m/s | 5.39 | vs | 5.36 | s | 5.37 | s/vs |
| 4.91 | w | 4.94 | vw | 4.92 | w | 4.92 | w/vw |
| 4.83 | w | 4.86 | w/vw | 4.83 | w | 4.84 | w/vw |
| 4.58 | w | 4.61 | vw | 4.60 | m | 4.62 | w/vw |
| 4.34 | vs | 4.37 | w | 4.35 | s | 4.35 | s |
| 4.24 | m | 4.27 | w | 4.25 | m/s | 4.26 | w |
| 4.02 | s | 4.04 | vs | 4.02 | vs | 4.03 | vs |
| 3.89 | w/vw | 3.92 | w/vw | 3.90 | w | 3.90 | w/vw |
| 3.72 | m/s | 3.77 | w | 3.74 | m/s | 3.74 | w |
| 3.64 | w/vw | 3.66 | vw | 3.64 | w | 3.65 | w/vw |
| 3.57 | w/vw | 3.59 | vw | 3.58 | m | 3.58 | w/vw |
| 3.50 | m | 3.53 | w | 3.51 | m | 3.51 | w |
| 3.46 | w | 3.48 | vw | 3.47 | m | 3.48 | w |
| 3.33 | w/vw | 3.35 | vw | 3.34 | w/vw | 3.34 | w/vw |
| 3.26 | vw | 3.28 | vw | 3.27 | vw | 3.27 | vw |
| 3.17 | m | 3.19 | w | 3.18 | m | 3.18 | w |
| 3.07 | m/w | 3.09 | m/w | 3.07 | m/w | 3.08 | m/w |
| 2.86 | vw | 2.88 | vw | 2.87 | vw | 2.87 | vw |
| 2.79 | vw | 2.80 | vw | 2.79 | vw | 2.79 | vw |
| 2.73 | w | 2.74 | w | 2.74 | w | 2.74 | w |
| 2.55 | w/vw | 2.57 | vw | 2.56 | w/vw | 2.56 | vw |
| 2.42 | vw | 2.43 | vw | 2.42 | vw | 2.42 | vw |

[1]Typical fluoxetine hydrochloride API
[2]Form A of fluoxetine hydrochloride prepared as taught hereinbelow.
[3]vw = very weak; w = weak; m = moderate; s = strong; and vs = very strong intensities.

Accordingly, x-ray powder diffraction serves as a useful tool for confirming the presence of fluoxetine hydrochloride, but is not a useful tool for differentiating among the various individual or mixtures of polymorphs of fluoxetine hydrochloride. However, when used in combination with differential scanning calorimetry (DSC), x-ray powder diffraction is used to confirm the presence of fluoxetine hydrochloride (see, e.g., Example 15), and DSC is used to confirm the presence of Form A, in pure and essentially pure form, and mixtures of fluoxetine hydrochloride polymorphs.

Figure 2:
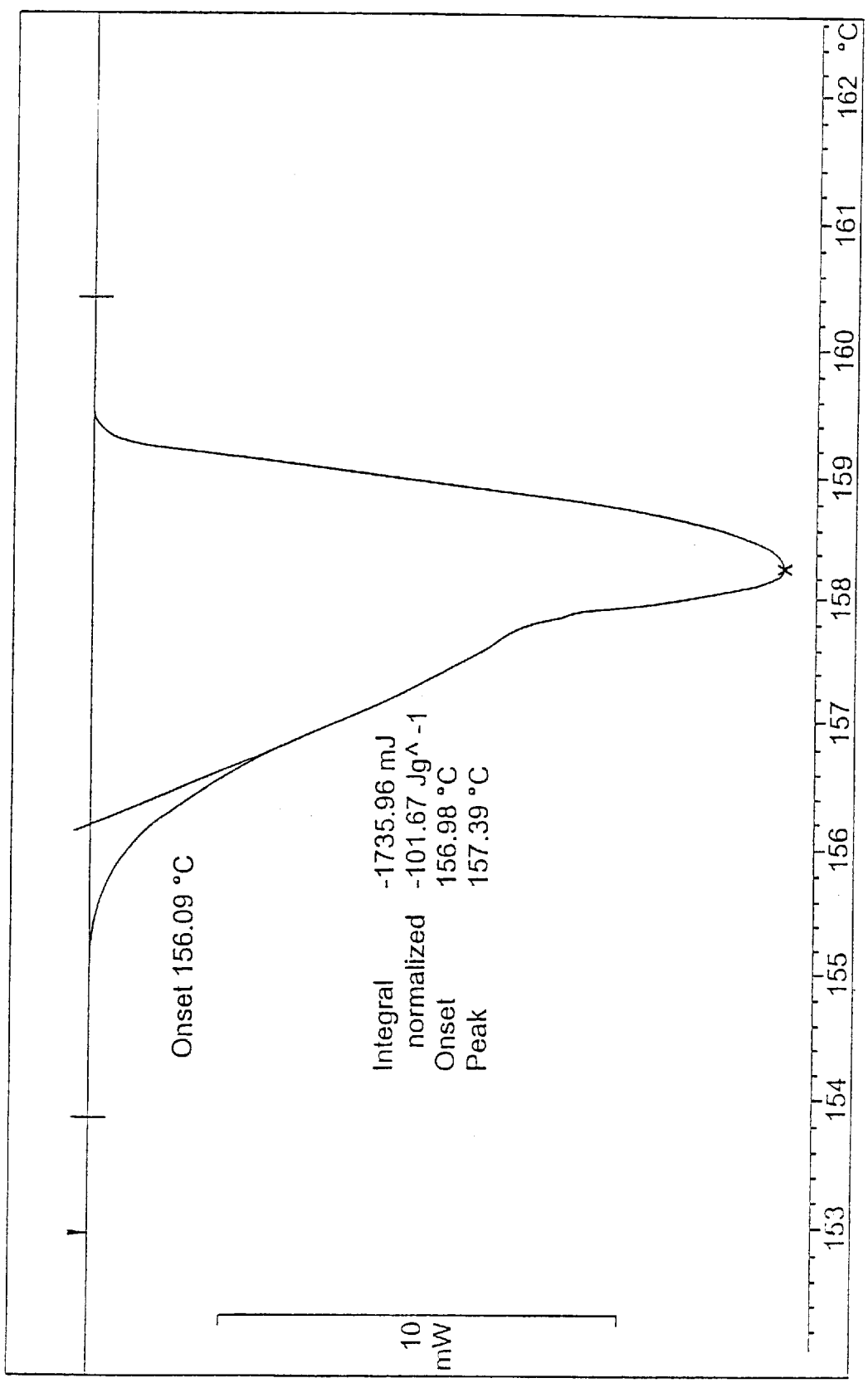
FIG. 2 shows the corresponding differential scanning calorimeter (DSC) thermogram for the fluoxetine hydrochloride API sample represented in the XRD pattern shown in FIG. 1.
Figure 4:
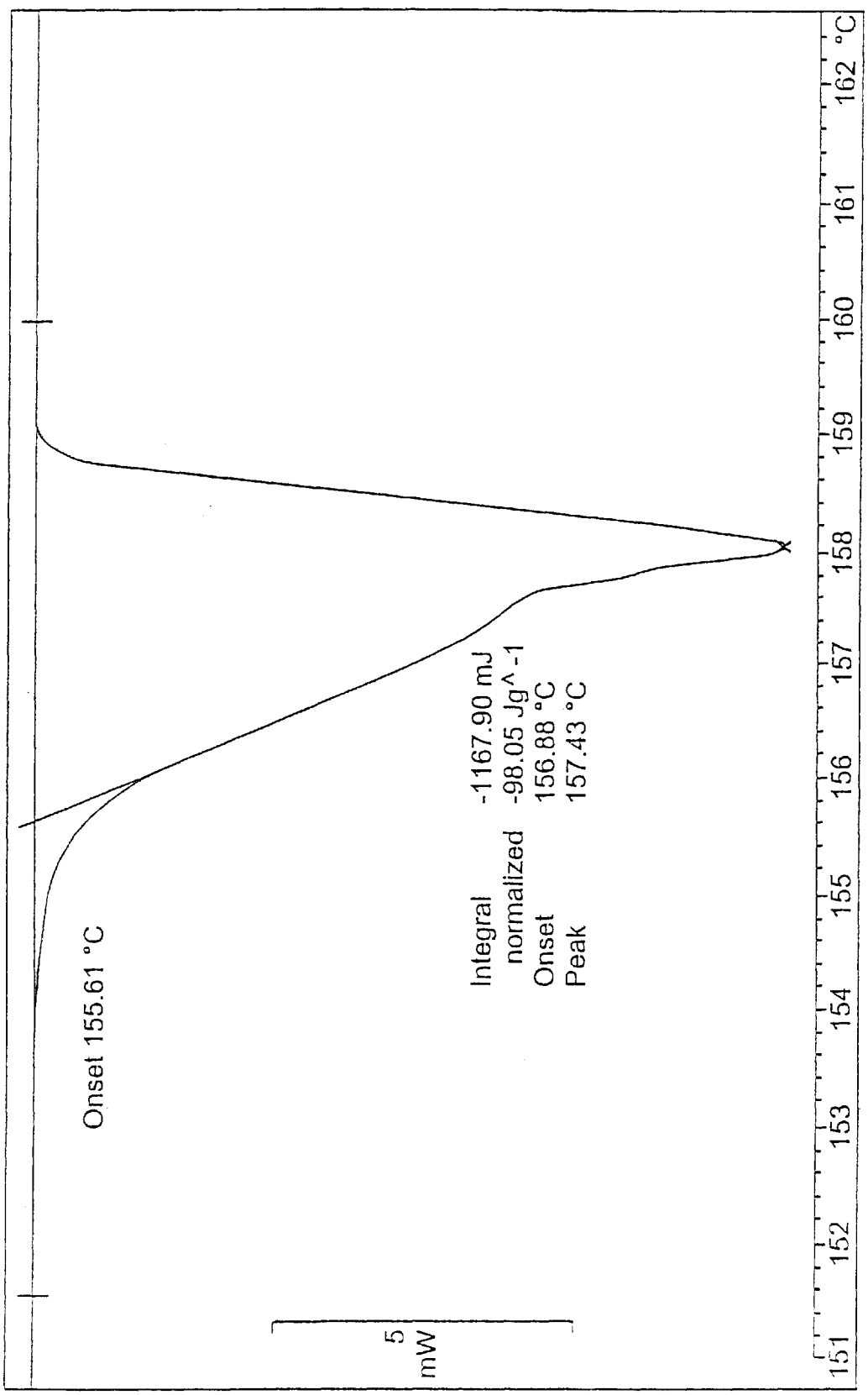
FIG. 4 shows the DSC thermogram for the fluoxetine hydrochloride API sample represented in the XRD pattern shown in FIG. 3.
Figure 6:
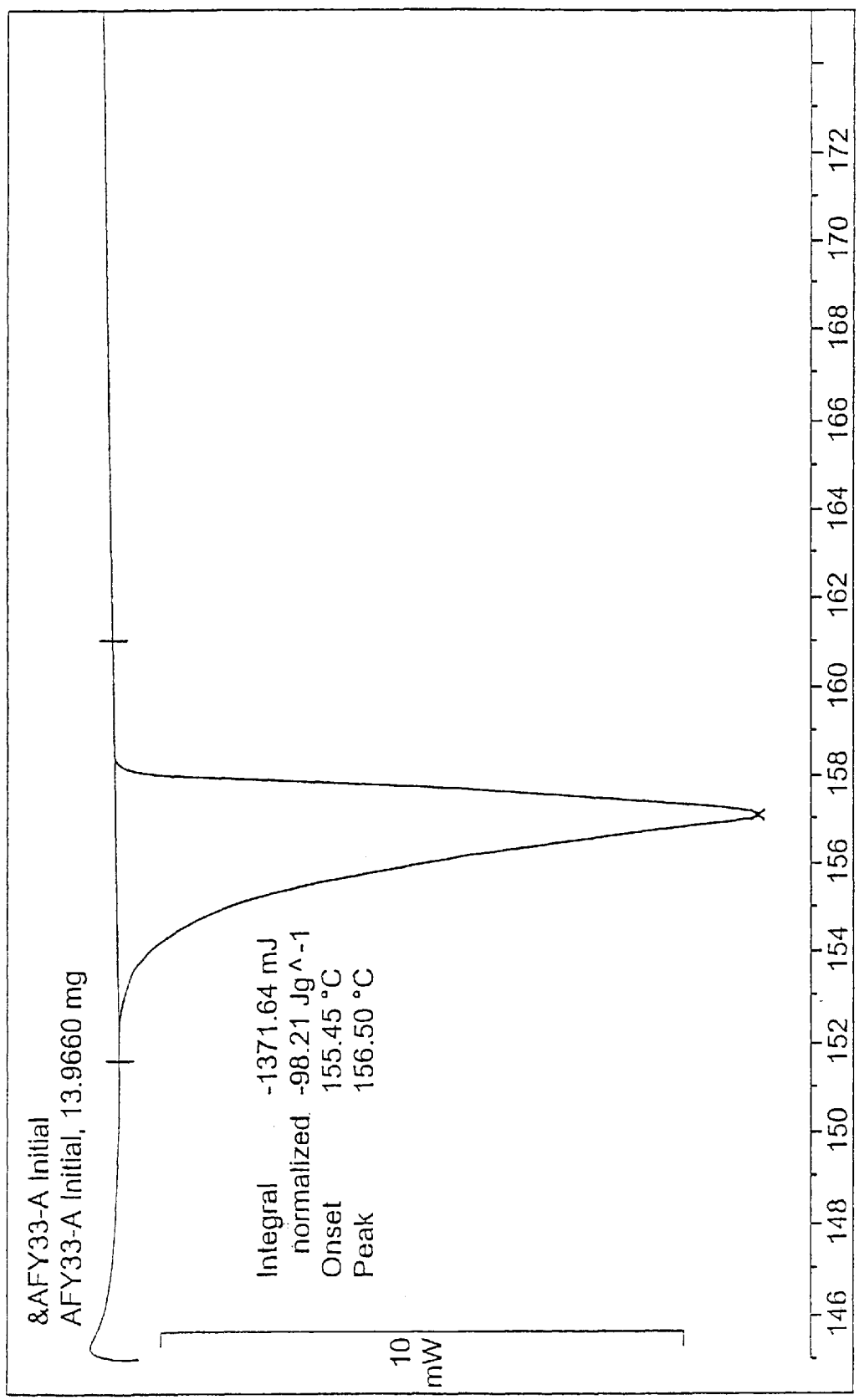
FIG. 6 shows the DSC thermogram for the Form A sample represented in the XRD pattern shown in FIG. 5.
Figure 8:
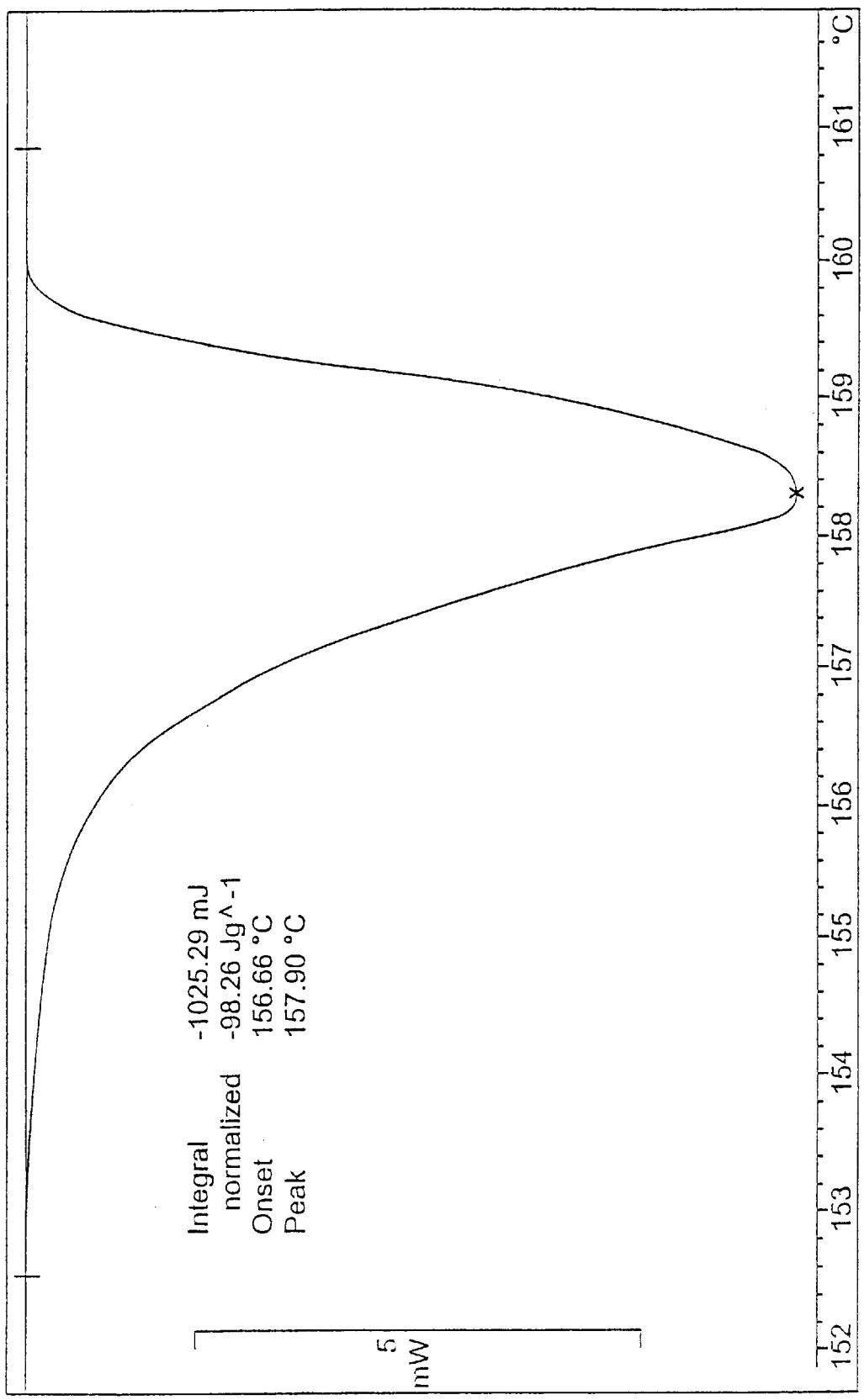
FIG. 8 shows the DSC thermogram for the Form A sample represented in the XRD pattern shown in FIG. 7.
Figure 9:
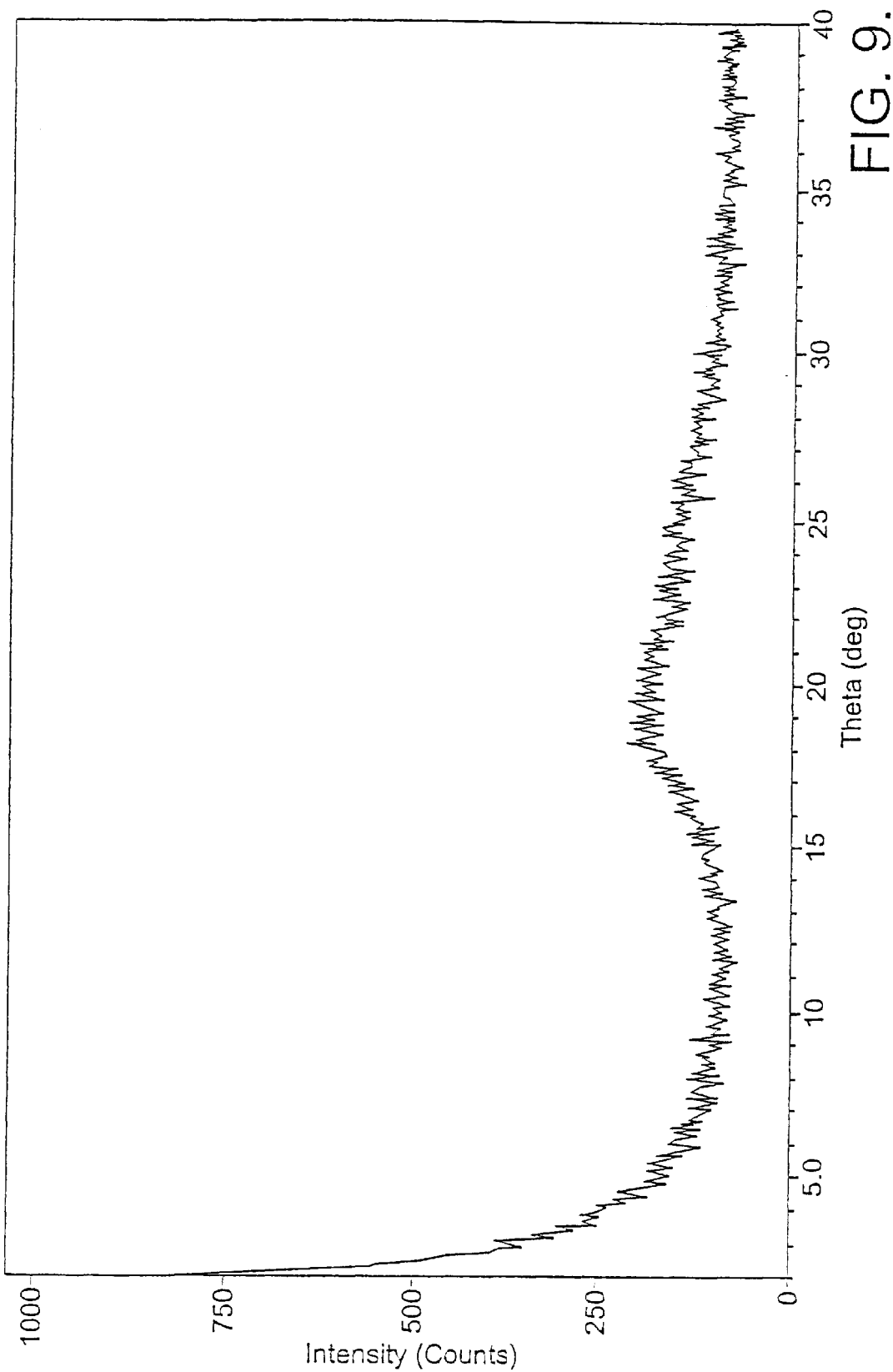
FIG. 9 shows an initial XRD pattern for amorphous fluoxetine hydrochloride prepared via the method taught herein.
Figure 10:
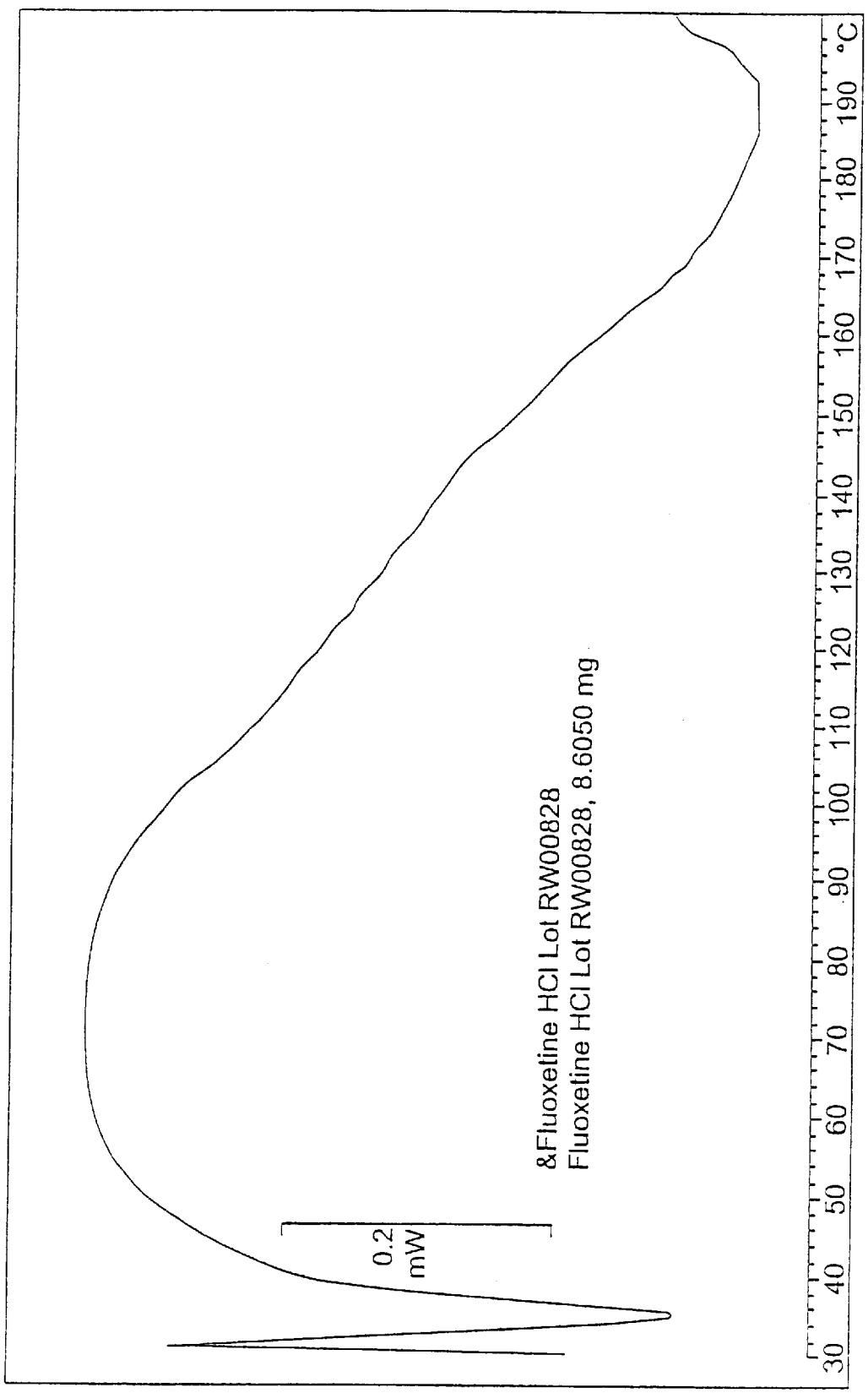
FIG. 10 shows the initial DSC thermogram from the amorphous fluoxetine hydrochloride sample represented in the XRD pattern shown in FIG. 9.
Figure 11:
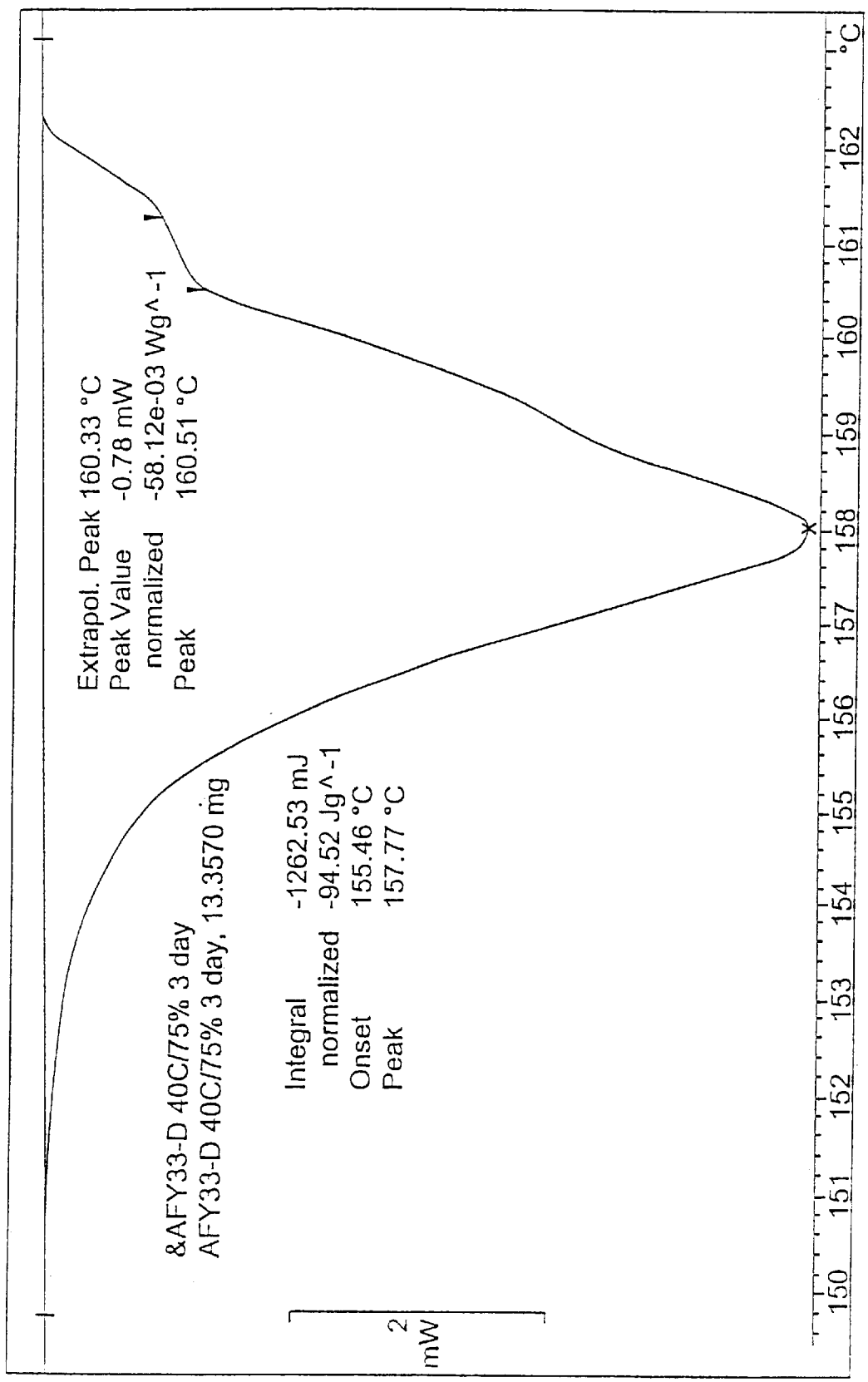
FIG. 11 shows a DSC thermogram for Forms A, D, and E, which formed within three days after pure Form A of fluoxetine hydrochloride was prepared via the recrystallization method taught herein when stored at 40° C. and 75% relative humidity.

Using the appropriately precise DSC method set forth in Example 12 herein, wherein the analysis is conducted at a maximum rate of 1° C. per minute, multiple levels of polymorph Forms A, B, and C each are typically present in fluoxetine hydrochloride API (FIGS. 2 and 4). When such API is prepared via any one of the methods of the present invention, recrystallization, slurry, and compression, and analyzed using said DSC method, a single endotherm occurring at a temperature range from about 155° C. to about 160° C., and more preferably from about 157° C. to about 159° C., confirms the presence of Form A of fluoxetine hydrochloride (FIGS. 6 and 8 for the compression and slurry methods, respectively). Interestingly, when such DSC method was used to analyze Form A prepared via such recrystallization method and placed under accelerated stability conditions (40° C. and 75% relative humidity) for less than one week, the presence of Form A was confirmed, but two additional polymorphs of fluoxetine hydrochloride, Forms D and E, were prepared (FIG. 11). Accordingly, the slurry method for preparing pure and essentially pure Form A is preferred, while the compression method is especially preferred.

For additional confirmation of the presence of Form of fluoxetine hydrochloride in pure form, single x-ray crystallography, x-ray powder diffraction, and differential scanning calorimetry can be used together.

Furthermore, x-ray powder diffraction and differential scanning calorimetry can be used to identify essentially pure Form A. The powder pattern for essentially pure Form A is consistent with those for fluoxetine hydrochloride API and pure Form A as taught herein. However, essentially pure Form A is further characterized by having at least two endotherms as determined by DSC run at a maximum rate of 1° C. per minute. Essentially pure Form A is defined by an increase in Form A and decrease of other polymorphs of fluoxetine hydrochloride compared to the starting material when prepared, for example, as taught herein, but the crystallization process is not permitted to run to completion which would form pure Form A. However, it is preferred that the amount of fluoxetine hydrochloride polymorphs other than Form A does not exceed an amount greater than about ten percent (w/w) and, more preferably, does not exceed an amount greater than about five percent (w/w).

For the purpose of this invention, the term "pure" refers to Form A of fluoxetine hydrochloride being in a concentration such that other fluoxetine polymorphs are present in amounts generally below limits detectable by conventional technology, particularly the Differential Scanning Calorimetry (DSC) method taught in Example 12 herein Although the present invention provides for pure and essentially pure Form A of fluoxetine hydrochloride, it is particularly preferred, of course, to eliminate all of the other polymorphic impurities to provide pure Form A of the present invention.

Fluoxetine hydrochloride API can be prepared by a multitude of processes known in the art (see e.g., U.S. Pat. Nos. 4,314,081; 5,166,437; and 5,225,585). The compositions of the present invention are preferably prepared by using such fluoxetine hydrochloride API as the staring material. The recrystallization and slurry methods set forth below can be used as the final steps in many crystallization processes in situ for the preparation of fluoxetine hydrochloride, without requiring a "recrystallization" processes, resulting in the preparation of Form A, preferably in pure and essentially pure form. Preferred methods for the preparation of Form A are set forth below, but are not intended to limit the scope of the present invention.

Preparation of Form A

I. Recrystallization Method. Fluoxetine hydrochloride API is recrystallized (or crystallized in situ, as the case may be) into Form A by dissolving such API in a suitable solvent in excess. Suitable solvents are those which are capable of dissolving fluoxetine hydrochloride so that a solution is formed, and include solvents across various classes including, for example, protic, aprotic, polar, and non-polar. Alcohol-based solvents are preferred and methanol is especially preferred. The resulting solution is filtered and permitted to recrystllize, most preferably at a fixed temperature, by evaporation. The temperature used for the evaporation step should be held constant at a temperature which permits the recrystallization of the starting material to Form A. A temperature range from about 0° C. to about 60° C. is preferred, while a temperature range from about 15° C. to about 40° C. is more preferred, and about ambient temperature is most preferred. This method has provided pure and essentially pure Form A of fluoxetine hydrochloride depending upon whether this recrystallization process is allowed to run to completion. However, this method is the least preferred of the methods taught herein. This method typically produces Form A, which, due to the method used, may transform to at least two more previously unidentified polymorphic forms of fluoxetine hydrochloride, designated as Forms D and E.

II. Slurry Method. Fluoxetine hydrochloride API is recrystallized (or crystallized in situ, as the case may be) into stable Form A by adding such API to a suitable solvent until a slurry is formed. Suitable solvents are those which are capable of sufficiently dissolving such API to form a slurry and establish a dynamic solubility equilibrium. Alcohol-based solvents are preferred and methanol is especially preferred. The resulting slurry is stirred until Form A is in pure or essentially pure form, as desired. Typically, the slurry is stirred for about two days depending upon batch size and solvent used, preferably at ambient temperature, and filtered. Most preferably, this process is run at a fixed temperature. For the preparation of pure Form A, it is preferred to allow this process to run to completion, as demonstrated by the preferred DSC method taught herein Acceptable temperature ranges are those which will permit the transformation of the staring material to Form A, while a temperature range from about 0° C. to about 60° C. is preferred, a temperature range from about 15° C. to about 40° C. is more preferred, and about ambient temperature is most preferred.

III. Compression Method. Particularly surprising was the discovery that Form A of fluoxetine hydrochloride can be prepared via compression. Various pieces of equipment may be used during the preparation of pharmaceutical products to provide a pressure of about 100 pounds per square inch (psi) to about 5000 psi, or greater. Such equipment includes, for example, hydraulic presses. Such equipment can provide sufficient pressure to convert the existing multiple polymorphic forms of fluoxetine hydrochloride to stable, pure or essentially pure Form A by regulating the amount of pressure used in this method. Preferably, at least about 100 psi is used. It is also preferred to use sufficient pressure without changing the other physical properties of Form A which are reasonably necessary for preparation of the respective drug product. Conduction of the relative purity of Form A prepared by this process is also confirmed using DSC.

Accordingly, the present invention provides, in part, pure and essentially pure Form A of fluoxetine hydrochloride, and methods for the preparation thereof. The present invention further provides methods for reducing, minimizing, and eliminating polymorphic contaminants (i.e., fluoxetine hydrochloride Forms B and C), and inhibiting the formation of other polymorphic forms of fluoxetine hydrochloride (i.e., Forms D and E).

It was also unexpectedly discovered that amorphous fluoxetine hydrochloride can be used as an intermediate for the preparation of Form A of the present invention. The starting material for this process, generally, is fluoxetine hydrochloride. Such starting material is heated to above the melting point thereof, then slowly cooled to about ambient temperature. It is preferred to heat such starting material to just beyond the melting point thereof (generally, just beyond about 155° C. to about 160° C.) to avoid over heating such starting material to the point that it decomposes in part or in whole. The sample initially remains in the amorphous state, as confirmed by x-ray powder diffraction, but recrystallized into Form A following nucleation. Nucleation can actively be induced (i.e., physically disturbing the sample) or passively induced by the use of natural forces by permitting the sample to be exposed to nucleation forces including, for example, dust particles, vibration, or air currents.

Accordingly, the present invention further provides amorphous fluoxetine hydrochloride, generally useful as an intermediate for the preparation of Form A of the present invention, and methods for preparing such Form A therefrom.

The present invention further provides methods of using Form A of fluoxetine hydrochloride, preferably in pure and essentially pure form, for inhibiting serotonin uptake in mammals comprising administering to a mammal requiring increased neurotransmission of serotonin an effective amount of one or more desired form(s) of fluoxetine hydrochloride of the present invention. Pure Form A is preferred. Disease states requiring such inhibition of serotonin uptake include, for example, depression, anxiety, alcoholism, chronic pain, eating disorders such as, for example, obesity and bulimia, and smoking cessation.

For the most effective administration of novel Form A of the present invention, it is preferred to prepare a pharmaceutical formulation preferably in unit dose form, comprising one or more of the active ingredients of the present invention and one or more pharmaceutically acceptable carrier, diluent, or excipient. As used herein, the term "active ingredient" refers to any of the embodiments set forth herein, particularly Form A of fluoxetine hydrochloride in pure or essentially pure form.

Such pharmaceutical formulation may, without being limited by the teachings set forth herein, include a solid form of the present invention which is blended with at least one pharmaceutically acceptable excipient, diluted by an excipient or enclosed within such a carrier that can be in the form of a capsule, sachet, tablet, buccal, lozenge, paper, or other container. When the excipient serves as a diluent, it may be a solid, semi-solid, or liquid material which acts as a vehicle, carrier, or medium for the active ingredient(s). Thus, the formulations can be in the form of tablets, pills, powders, elixirs, suspensions, emulsions, solutions, syrups, capsules (such as, for example, soft and hard gelatin capsules), suppositories, sterile injectable solutions, and sterile packaged powders.

Examples of suitable excipients include, but are not limited to, starches, gum arabic, calcium silicate, microcrystalline cellulose, polyvinylpyrrolidone, cellulose, water, syrup, and methyl cellulose. The formulations can additionally include lubricating agents such as, for example, talc, magnesium stearate and mineral oil; wetting agents; emulsifying and suspending agents; preserving agents such as methyl- and propyl-hydroxybenzoates; sweetening agents; or flavoring agents. Polyols, buffers, and inert fillers may also be used. Examples of polyols include, but are not limited to: mannitol, sorbitol, xylitol, sucrose, maltose, glucose, lactose, dextrose, and the like. Suitable buffers encompass, but are not limited to, phosphate, citrate, tartrate, succinate, and the like. Other inert fillers which may be used encompass those which are known in the art and are useful in the manufacture of various dosage forms. If desired, the solid pharmaceutical compositions may include other components such as bulking agents and/or granulating agents, and the like. The compositions of the invention can be formulated so as to provide quick, sustained, controlled, or delayed release of the active ingredient after administration to the patient by employing procedures well known in the art.

In certain embodiments of the invention, the active ingredient(s) may be made into the form of dosage units for oral administration. The active ingredient(s) may be mixed with a solid, pulverant carrier such as, for example, lactose, saccharose, sorbitol, mannitol, starch, amylopectin, cellulose derivatives or gelatin, as well as with an antifriction agent such as for example, magnesium stearate, calcium stearate, and polyethylene glycol waxes. The mixture is then pressed into tablets or filled into capsules. If coated tablets, capsules, or pulvules are desired, such tablets, capsules, or pulvules may be coated with a concentrated solution of sugar, which may contain gum arabic, gelatin, talc, titanium dioxide, or with a lacquer dissolved in the volatile organic solvent or mixture of solvents. To this coating, various dyes may be added in order to distinguish among tablets with different active compounds or with different amounts of the active compound present Soft gelatin capsules may be prepared in which capsules contain a mixture of the active ingredient(s) and vegetable oil or non-aqueous, water miscible materials such as, for example, polyethylene glycol and the like. Hard gelatin capsules may contain granules or powder of the active ingredient in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are gently ground or sieved to a desired particle size, and a binding agent is homogenized and suspended in a suitable solvent. The active ingredient(s) and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for a pre-determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size.

In the event that the above formulations are to be used for parenteral administration, such a formulation typically comprises sterile, aqueous and non-aqueous injection solutions comprising one or more active ingredients for which preparations are preferably isotonic with the blood of the intended recipient. These preparations may contain anti-oxidants, buffers, bacteriostats, and solute; which render the formulation isotonic with the blood of the intended recipient Aqueous and non-aqueous suspensions may include suspending agents and thickening agents. The formulations may be present in unit-dose or multi-dose containers, for example, sealed ampules and vials. Extemporaneous injection solutions and suspensions may be prepared from sterile powders, granules, and tablets of the kind previously described.

Liquid preparations for oral administration are prepared in the form of solutions, syrups, or suspensions with the latter two forms containing, for example, active ingredient(s), sugar, and a mixture of ethanol, water, glycerol, and propylene glycol. If desired, such liquid preparations contain coloring agents, flavoring agents, and saccharin. Thickening agents such as carboxymethylcellulose may also be used.

As such, the pharmaceutical formulations of the present invention are preferably prepared in a unit dosage form, each dosage unit containing from about 5 mg to about 200 mg, more usually from about 10 mg to about 40 mg of the active ingredient(s). In liquid form, dosage unit contains from about 5 to about 200 mg, more usually about 1 mg to about 40 mg of active ingredient(s). The term "unit dosage form" refers to physically discrete units suitable as unitary dosages for human subjects/patients or other mammals, each unit containing a predetermined quantity of active ingredient calculated to produce the desired therapeutic effect, in association with preferably, at least one pharmaceutically acceptable carrier, diluent, or excipient.

The following examples are illustrative and are not intended to limit the scope of the invention in any way.

Formulation 1
Hard gelatin 20 mg capsules are prepared using the following ingredients:

|  | Quantity (mg/capsule) |
| --- | --- |
| active ingredient ethanedioate | 20 |
| starch, dried | 200 |
| magnesium stearate | 10 |
| Total | 230 |

The above ingredients are mixed and filled into hard gelatin capsules in 230 mg quantities.

Formulation 2
A 20 mg tablet is prepared using the ingredients below:

|  | Quantity (mg/tablet) |
| --- | --- |
| active ingredient | 20 |
| cellulose, microcrystalline | 400 |
| silicon dioxide, fumed | 10 |
| stearic acid | 5 |
| Total | 435 | the components are blended and compressed to form tablets each weighing 435 mg.

Formulation 3
Tablets each containing 20 mg of active ingredient are made as follows:

| active ingredient | 20 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 110 mg |

The active ingredient, starch and cellulose are passed through a No. 45 mesh U.S. sieve and mixed thoroughly. the solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 110 mg.

Formulation 4
Capsules each containing 10 mg of medicament are made as follows:

| active ingredient | 10 mg |
| --- | --- |
| starch | 59 mg |
| microcrystalline cellulose | 59 mg |
| magnesium stearate | 2 mg |
| Total | 130 mg |

The active ingredient, cellulose, starch and magnesium stearate are blended, passed through a No. 45 mesh U.S. seive, and filled into hard gelatin capsules in 130 mg quantities.

Formulation 5
Suspensions each containing 20 mg of medicament per 5 ml dose are made as follows:

| active ingredient | 20 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 6
An intravenous formulation may be prepared as follows:

| active ingredient | 100 mg |
| --- | --- |
| isotonic saline | 1000 ml |

The solution of the above ingredients is administered intravenously at a rate of 1 ml per minute to a subject suffering from depression.

The following examples are intended to illustrate the invention, and are not to be construed as limiting the scope of the present invention.

EXAMPLE 1

Form A via the recrystallization method. To a 20 mL beaker containing 10 mL of methanol was added an amount of fluoxetine hydrochloride API such that the resulting suspension was at or near the saturation point The suspension was then magnetically stirred for about 15 minutes and filtered through a 0.45 μm polytrifluoroethylene ("PTFE") filter. The resulting solution was allowed to stand undisturbed at ambient temperature until the solvent evaporated (about 1 to 2 days). X-ray powder diffraction (XRD) confirmed the end product is fluoxetine hydrochloride, and differential scanning calorimetry (DSC) confirmed the presence of pure Form A polymorph of fluoxetine hydrochloride.

EXAMPLE 2

Form A via the recrystallization method. The process set forth in Example 1 above was used, but water rather than methanol was used as a solvent XRD confirmed the end product is fluoxetine hydrochloride, and DSC confirmed the presence of pure Form A polymorph of fluoxetine hydrochloride.

EXAMPLE 3

Form A via the recrystallization method. The process set forth in Example 1 above was used, but dimethylformamide rather than methanol was used as a solvent. XRD confirmed the end product is fluoxetine hydrochloride, and DSC confirmed the presence of pure Form A polymorph of fluoxetine hydrochloride.

EXAMPLE 4

Form A via the slurry method. To a 20 mL beaker containing 10 mL of methanol was added sufficient fluoxetine hydrochloride API, in excess, to form a slurry. The resulting slurry was magnetically stirred for about 48 hours at ambient temperature. The slurry was filtered (using a 0.45 μm PTFE filter) and the collected solid material was dried under a vacuum at ambient temperature for about 4 hours. XRD confirmed the end product is fluoxetine hydrochloride, and DSC confirmed the presence of pure Form A polymorph of fluoxetine hydrochloride.

EXAMPLE 5

Form A via the compression method. A 100 mg sample of fluoxetine hydrochloride API was placed in a dye and compressed by a Carver Press (Fred S. Carver, Inc.; Menomonee Falls, Wis.) at about 100 psi to obtain a pellet The pellet was broken apart using a scalpel and tested. XRD confirmed the end product is fluoxetine hydrochloride, and DSC confirmed the presence of pure Form A polymorph of fluoxetine hydrochloride.

EXAMPLES 6–9

Form A via the compression method. Using the procedure set forth in Example 5 above, fluoxetine hydrochloride API samples were compressed at 1000, 2000, 4000, and 4500 psi. XRD confirmed that each sample is fluoxetine hydrochloride, and DSC confirmed the presence of pure Form A polymorph of fluoxetine hydrochloride.

EXAMPLE 10

Form A via amorphous fluoxetine hydrchloride. A sample of 50 mg of fluoxetine hydrochloride API was heated by hot stage microscopy to 170° C. until the entire sample entered the "glass" phase. The sample was allowed to cool at ambient temperature. XRD confirmed the resulting fluoxetine hydrochloride is in amorphous form, and no melting point was observed using DSC. Following nucleation, XRD and DSC confirmed that the resulting material is crystalline fluoxetine hydrochloride as Form A thereof.

EXAMPLE 11

Differential Scanning Calorimetry for fluoxetine hydrochloride. A sample of about 10 mg was placed in a sealed aluminum sample holder and was heated from 30° C. to 180° C., at 10° C. per minute under a 40 mL per minute nitrogen purge, using a Mettler-Toledo (Columbus, Ohio) DSC821$^e$ differential scanning calorimeter with Star$^e$ software package (also from Mettler-Toledo). Endotherms demonstrated the presence of at least two polymorphs in fluoxetine hydrochloride API, designated Forms A and B of fluoxetine hydrochloride API. However, the resolution was less than desired, and the method set forth in Example 12 herein was developed as a required method.

EXAMPLE 12

Differential Scanning Calorimetry for fluoxetine hydrochloride. The method described in Example 11 was used, except the heating rate was changed from 10° C. per minute to a heating rate of 1° C. per minute from 145° C. to 175° C. The improved resolution from use of this method resulted in the observation of at least three polymorphs of fluoxetine hydrochloride API, designated Forms A, B, and C fluoxetine hydrochloride API.

EXAMPLE 13

Differential Scanning Calorimetry for pure Form A of fluoxetine hydrochloride. The method used in Example 12 was used, except the fluoxetine hydrochloride from Examples 2 and 3 were tested rather than fluoxetine hydrochloride API. A single endotherm from about 155° C. to about 160° C. confirmed the presence of a single fluoxetine hydrochloride polymorph, identified as pure Form A via the method taught in Example 14.

EXAMPLE 14

Determination of the single crystal structure of Form A of fluoxetine hydrochloride. Single Crystal X-Ray Diffraction was used to determine the single crystal structure of Form A of fluoxetine hydrochloride. Without being bound to theory, it is believed that a crystalline material diffracts X-rays due to the constructive and destructive interference of the scattering of X-rays from the atoms of the molecule within the crystal lattice. The intensity and positions of the diffraction spots produced by the crystal is capable of generating structural information about the locations of the atoms in the molecule of a crystal.

In this instance, a single crystal of the material to be examined is mounted at the end of a glass fiber. The crystal is aligned in the diffractometer in a specific orientation. The diffraction spots are measured, then the crystal is rotated to the next position The above sequence is then repeated until thousands of individual diffraction spots are measured and recorded. The diffraction spots are then analyzed and the data phased to generate an electron density map from which a molecular structure of the molecule is uniquely determined. The X-ray diffraction data is generated using either a Nonius CAD4 diffractometer or a Nonius Kappa CCD diffractometer made commercially available by Nonius Corporation of Delft, Netherlands. Pure Form A of fluoxetine hydrochloride prepared in the methods taught herein is characterized by the following single crystallization parameters:

| | |
|---|---|
| crystal class | orthorhombic |
| space groups | Pbca (#61) |
| a (Å) | 10.3754 (4) |
| b (Å) | 10.4603 (2) |
| c (Å) | 32.3412 (12) |
| V (Å$^3$) | 3510.0 (3) |
| d calc (g/cm$^3$) | 1.31 |
| R, R$_w$ | 0.038, 0.038 |

EXAMPLE 15

X-ray Powder Diffraction for fluoxetine hydrochloride. A sample of about 50 mg of fluoxetine hydrochloride was placed on a zero-background sample plate and analyzed using copper Kα Radiation (λ=1.5418 Å) from 2 to 40 degrees in 2-theta at 2.4 degrees per minute. A Siemens D500 automated diffractometer (Munich, Germany) with MDI software (Livermore, Calif.) was used for the analysis and processing of the data That which is claimed is:

1. Form A of fluoxetine hydrochloride prepared by a process comprising heating substantially crystalline fluoxetine hydrochloride past the melting point thereof until melted fluoxetine hydrochloride is formed, cooling said melted fluoxetine hydrochloride under conditions which yield amorphous fluoxetine hydrochloride, and nucleating said amorphous fluoxetine hydrochloride to initiate transformation to said Form A of fluoxetine hydrochloride.

* * * * *